(12) United States Patent
Respass et al.

(10) Patent No.: US 10,918,087 B2
(45) Date of Patent: Feb. 16, 2021

(54) INTELLIGENT ANIMAL CONTAINMENT SYSTEM

(71) Applicants: Robert Michael Respass, Clarksville, TN (US); Amanda Spicer, Belleville, MI (US)

(72) Inventors: Robert Michael Respass, Clarksville, TN (US); Amanda Spicer, Belleville, MI (US)

( * ) Notice: Subject to any disclaimer, the term of this patent is extended or adjusted under 35 U.S.C. 154(b) by 225 days.

(21) Appl. No.: 15/953,667

(22) Filed: Apr. 16, 2018

(65) Prior Publication Data

US 2018/0295812 A1 Oct. 18, 2018

Related U.S. Application Data

(60) Provisional application No. 62/486,678, filed on Apr. 18, 2017.

(51) Int. Cl.

| | | |
|---|---|---|
| *A01K 15/04* | (2006.01) | |
| *A01K 27/00* | (2006.01) | |
| *A01K 29/00* | (2006.01) | |
| *A61M 21/02* | (2006.01) | |
| *A01K 11/00* | (2006.01) | |
| *A61B 5/145* | (2006.01) | |
| *A61B 5/024* | (2006.01) | |
| *A61B 5/021* | (2006.01) | |
| *A61B 5/01* | (2006.01) | |
| *A61M 21/00* | (2006.01) | |

(52) U.S. Cl.
CPC ............ *A01K 15/04* (2013.01); *A01K 27/009* (2013.01); *A01K 29/005* (2013.01); *A61M 21/02* (2013.01); *A01K 11/008* (2013.01); *A61B 5/01* (2013.01); *A61B 5/021* (2013.01); *A61B 5/024* (2013.01); *A61B 5/14532* (2013.01); *A61B 5/14542* (2013.01); *A61M 2021/0027* (2013.01)

(58) Field of Classification Search
CPC .... A01K 15/04; A01K 27/009; A01K 11/008; A01K 11/006; A01K 29/005; A01K 15/023; A01K 15/02
USPC .............. 119/712, 718–721, 908; 340/573.1, 340/573.3, 573.4, 572.1
See application file for complete search history.

(56) References Cited

U.S. PATENT DOCUMENTS

| | | | |
|---|---|---|---|
| 6,700,492 B2 * | 3/2004 | Touchton | A01K 15/02 |
| | | | 119/721 |
| 7,173,535 B2 * | 2/2007 | Bach | A01K 15/023 |
| | | | 119/712 |
| 7,259,718 B2 * | 8/2007 | Patterson | G01S 13/878 |
| | | | 342/463 |
| 8,297,233 B2 * | 10/2012 | Rich | A01K 15/023 |
| | | | 119/721 |
| 8,726,846 B2 | 5/2014 | Dutcher et al. | |

(Continued)

*Primary Examiner* — Trinh T Nguyen
(74) *Attorney, Agent, or Firm* — Hall Estill Attorneys at Law; Tyler Mantooth

(57) ABSTRACT

An animal containment system can intelligently control an animal with at least an animal device attached to an animal. Activating the animal device allows for detection of the position of the animal. A controller of the animal device can use the animal device to detect if the animal is physically positioned outside of a first predetermined containment area. The controller can then execute a containment strategy with the animal device that activates a speaker of the animal device in response to the detected animal position.

16 Claims, 3 Drawing Sheets

(56) References Cited

U.S. PATENT DOCUMENTS

| | | |
|---|---|---|
| 8,779,952 B1 | 7/2014 | Zortea |
| 8,933,776 B2 | 1/2015 | Dua et al. |
| 9,101,113 B2 | 8/2015 | Rich et al. |
| 9,258,982 B1 | 2/2016 | Golden |
| 9,277,734 B1 | 3/2016 | Paradis |
| 9,439,396 B2 | 9/2016 | Namm |
| 9,485,963 B2 | 11/2016 | Shani et al. |
| 9,615,545 B2 | 4/2017 | Rich et al. |
| 2013/0092099 A1 | 4/2013 | Hardi et al. |
| 2015/0022329 A1 | 1/2015 | Shani et al. |
| 2015/0373951 A1* | 12/2015 | Kelly .................. A01K 27/009 119/719 |
| 2017/0172136 A1 | 6/2017 | LaRue |

\* cited by examiner

INTELLIGENT ANIMAL CONTAINMENT SYSTEM

RELATED APPLICATION

The present application makes a claim of domestic priority to U.S. Provisional Patent Application No. 62/486,678 filed Apr. 18, 2017, the contents of which are hereby incorporated by reference.

SUMMARY

An intelligent animal containment system, in accordance with some embodiments, has an animal device attached to an animal. The animal device has a controller configured to execute a containment strategy that activates a speaker of the animal device in response to detection of the animal being physically positioned outside of a predetermined containment area.

Other embodiments arrange an intelligent animal containment system with an animal device attached to an animal. Activation of the animal device allows for detection of the position of the animal. A controller of the animal device can use the animal device to detect if the animal is physically positioned outside of a first predetermined containment area. The controller then executes a containment strategy with the animal device that activates a speaker of the animal device in response to the detected animal position.

At least one animal can be contained with assorted embodiments of an intelligent animal containment system that activates an animal device attached to an animal and then uses the animal device to predict the animal will physically cross a predetermined containment area. The controller subsequently executes a containment strategy with a controller of the animal device where a speaker of the animal device is activated.

DETAILED DESCRIPTION

Controlling and containing animals in a predefined area has been a continued goal of commercial, agricultural, and residential consumers since the dawn of fences centuries ago. While fencing technology has gradually advanced to provide more robust containment means, very little was possible to locate and redirect an animal that had somehow left a fenced area. However, advancements in computing technology has allowed circuitry to be positioned on an animal, such as via a collar or jacket.

Accordingly, an intelligent animal containment system, in accordance with some embodiments, can detect when an animal has left a containment area and execute actions that direct the animal to return to the containment area. The ability to predefine a containment area electronically minimizes the importance of a physical fence while the execution of a containment strategy by an animal device can mitigate injury, death, and loss of animals that have strayed from the containment area. Connection of an animal device to a separate computing device allows the animal device to be customized over time and adapt to logged animal conduct by taking proactive actions in an effort to mitigate adverse predicted animal actions.

Figure 1:
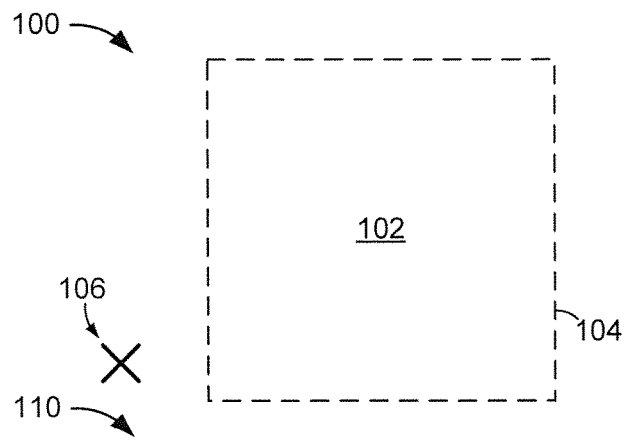
FIG. 1 represents an example environment in which various embodiments may be practiced.

FIG. 1 illustrates a top view line representation of an example environment 100 where various embodiments of the present disclosure can be practiced. The environment 100 can have one or more containment regions 102 that are electronically defined and enforced. That is, the containment region 102 does not require any corresponding physical structure, such as a fence, body of water, or geographical feature, but may have at least one structure 104.

The containment region 102 may be closed, as shown, or open, as defined by any size and shape. As a non-limiting example, the containment region 102 may have one or more linear sides and/or one or more continuously curvilinear sides that define a symmetric, asymmetric, open, or closed area. The containment region 102 can interact with an animal device 106 that is attached to an animal to identify various positional, medical, and behavioral characteristics about the animal. The animal device 106 can be configured to detect when the animal is outside of the containment region 102. Such positional awareness allows the animal device to intelligently administer corrective measures to control and redirect the animal within the containment region 102.

Figure 2:
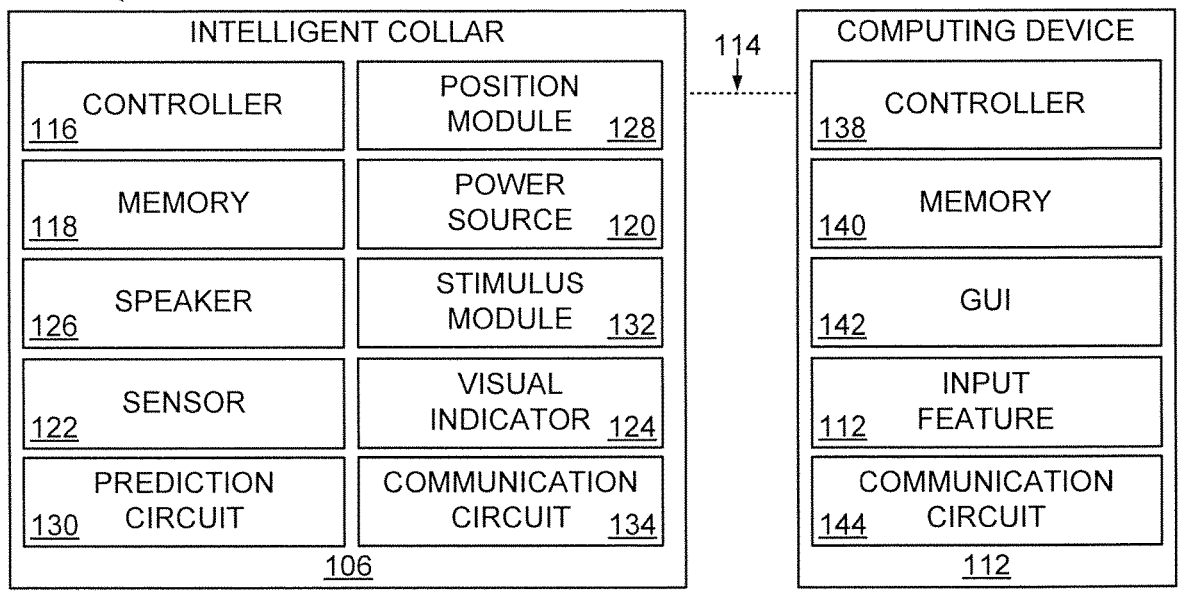
FIG. 2 displays block representation of an example intelligent animal containment system that can be employed in the environment of FIG. 1.

FIG. 2 depicts a block representation of an example animal containment system 110 that can operate in the environment of FIG. 1 in accordance with some embodiments. The system 110 can have any number of animal devices 106 that are physically separated from one or more computing devices 112 while being electronically connected via a wired and/or wireless data pathway 114. A wireless connection between each animal device 106 and the computing device(s) 112 allows the animal device(s) 106 to remain attached to an animal while being accessed and manipulated by the computing device 112.

It is noted that the animal device 106 is not limited in shape, size, position, or physical attachment to an animal. As such, an animal device may be collar with a physical loop around the neck of an animal or may be a vest, headband, ear tag, or component implanted under the animal's skin. Regardless of the physical arrangement of the animal device 106, electrical circuitry of the animal device 106 can consist of at least a local controller 116, such as a microprocessor or programmable processor, connected to a local non-volatile memory 118, such as a hard disc drive or solid-state memory array.

An animal device 106 can contain one or more internal power sources 120, such as a battery or rechargeable power cell, that provide electrical power to conduct a diverse variety of computing and animal conduct gathering operations. Although not required or limiting, some embodiments utilize the power source 120 to activate one or more sensors 122, such as an optical, proximity, vibration, or magnetic sensor. A sensor 122 may also be configured as biometric circuitry to provide medical information about the animal, such as heartrate, blood pressure, blood sugar, or body temperature.

One or more visual indicators 124 may also be powered by the power source 120. A visual indicator 124 can be lights or activated visual cues, such as a flag, that identifies the location of the animal. It is contemplated that the visual indicator 124 can further assist in slowing the animal, as in the case with a parachute. Visual cues may be accompanied by one or more audible indicators from at least one speaker 126. An audible indicator can consist of static or dynamic frequencies that may, or may not be within the audible range of the animal, or a human user.

The animal device 106 may consist of a positioning module 128 that continuously, sporadically, or routinely identifies the physical location of the animal device 106 on Earth. The positioning module 128 may consist of global positioning circuitry (GPS) that communicates with an extraterrestrial satellite along with other locational circuitry, such as sonar, radar, and wireless network beacon protocol. The physical position and biographical characteristics of the animal can be logged over time by the local controller 116 in the local memory 118, which allows a prediction module 130 to analyze and interpret the logged data to predict future animal behavior.

While not required or limiting, an animal device 106 may comprise a stimulus module 132 that can provide artificial stimulation to the animal. For example, the stimulus module 132 can consist of a power regulator that can shock the animal with electrical energy or a pattern generator that can expose the animal to visual and/or audible patterns designed to calm the animal. The ability to intelligently activate one or more visual and audible indicators along with one or more artificial stimuli allows the animal device 106 to control the animal to a certain extent while indicating to human users of the animal's position and biological state.

The local memory 118 can store software that follows a predetermine routine of visual/auditory indicators and/or stimuli as directed by the local controller 116. However, static software can be rigid and provide narrow practical usability for different containment regions, types of animals, and animal personalities. Hence, assorted embodiments continuously or sporadically connect a communication circuit 134 of the animal device 106 to a communication circuit 136 of the computing device 112. The computing device 112 may be a portable device, such as a smartphone, tablet computer, laptop computer, or smartwatch, or a fixed computer, such as a desktop computer, network server, or network node.

A device controller 138 provides computing capabilities, such as the generation, alteration, and transfer of data, into, and out of, a device memory 140. The device memory 140, in some embodiments, consists of long-term non-volatile memory along with short term cache memory that may be volatile or non-volatile. The device controller 138 can utilize software, firmware, and data stored in the device memory 140 to operate a graphical user interface (GUI) 142. The GUI 142 can be provided via a screen positioned anywhere, such as a watch, glasses, or phone.

The GUI 142 may be accessed and manipulated by one or more input features 144. For instance, the computing device 112 may have a touchscreen that serves to display the GUI 142 and allow for user manipulation of the GUI 142. It is contemplated that the computing device 112 is concurrently connected to multiple different types of input features 144, such as a keyboard, retinal tracker, stylus, mouse, or haptic surface, to allow a user to access and manipulate the content of the GUI 142.

Figure 3:
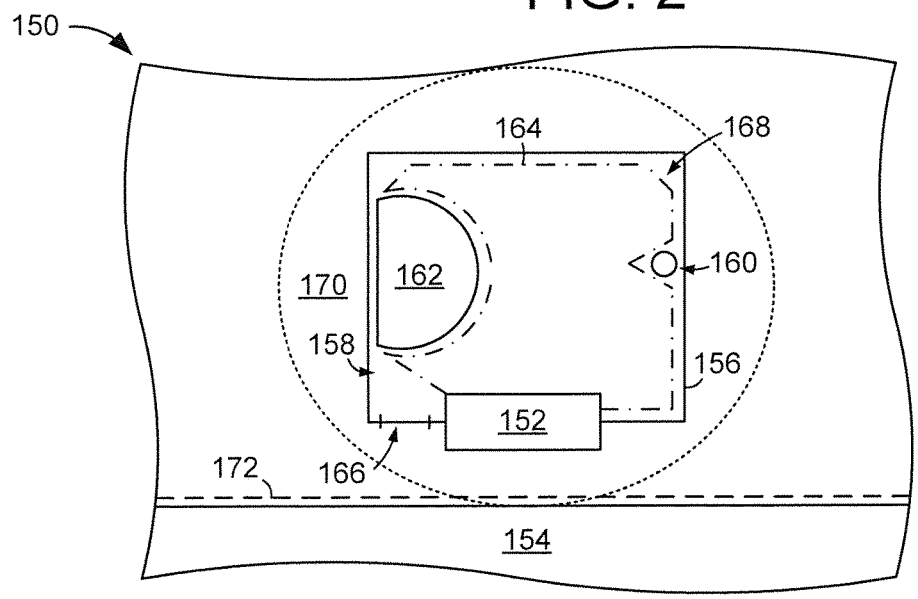
FIG. 3 is a line representation of portions of an example intelligent animal containment system configured and operated in accordance with some embodiments.

In accordance with various embodiments, software stored in the device memory 140, executed by the device controller 138, and accessed by the input feature(s) 144 via the GUI 142 allows a user to create a customized containment plan that utilizes some, or all, of the capabilities of the animal device 106 to monitor and control an animal wearing the animal device 106. FIG. 3 displays a top view line representation of an example containment plan 150 created and executed by the system 110 of FIG. 2 in the environment 100 of FIG. 1. The illustrated environment of FIG. 3 has a building 152 separated from a road 154. A fence 156 continuously extends from the building 152 and encloses a fenced region 158 where a tree 160 and pool 162 are located.

Historically, a user could place a physical barrier, such as an electronic fence or hotwire, to define where they wanted an animal to stay within. In yet, animals can evade such physical barriers, along with the fence 156 unbeknownst to a user. It is contemplated that tracking hardware may be attached to an animal to provide a current physical location, but such systems are limited in the capability to intelligently activate visual and audible indicators along with stimuli that can control and redirect an animal. As a result, past systems fail to fully utilize the computing power of local 116 and device 138 controllers to recognize and adapt to changing conditions to keep an animal safe.

As shown in FIG. 3, a user can create a virtual fence 164 that has an asymmetrical shape and accommodates for features where an animal is not wanted, such as around the tree 160 or pool 162. The virtual fence 164 is configured to prevent an animal from reaching a gate 166, climbing in corners 168 of the physical fence 156, or digging around any of the periphery of the physical fence 156. The virtual fence 164 can correspond with a first level of a containment plan in which a predetermined visual indicator, audible indicator, and/or physical stimulus is applied to the animal once the animal device detects the animal has traveled beyond the bounds of the virtual fence 156.

It is contemplated that the animal containment system can gradually, suddenly or in a step-like manner increase intensity of visual, audible, or physical stimuli to the animal as the animal approaches the virtual fence 156. That is, stimuli and/or indicators can begin before the animal actually reaches the virtual fence 156. In other embodiments, no indicators or stimuli are applied until the animal reaches the virtual fence 156 where physical stimuli are increased based on distance from the virtual fence 156. In other words, the virtual fence 156 can demarcate where indicators and/or stimuli begin and the animal's position relative to the fence 156 triggers the intensity of the indicators and/or stimuli.

In yet another non-limiting embodiment, a user can designate multiple different virtual fences that respectively correspond with different responses to an animal reaching, or crossing, the respective boundaries. For instance, approaching and/or crossing the first virtual fence 156 can trigger the animal device to activate a first stimulus, such as a minor electrical shock, that in increased in intensity until reaching, or crossing, a second virtual fence 170 where additional, and different, audible indicators are activated. Such audible indicators may be a high pitch whistle to startle the animal or the user's voice speaking a pre-recorded message, such as "come home" or the animal's name.

Any number of virtual fences can be created by a user with the respective fences potentially intersecting. A third virtual fence 172 is shown in FIG. 3 as a linear boundary proximal the road 154 that can be programmed to activate multiple visual indicators, such as a flag along with lights, to alter oncoming vehicles of the loose animal while also altering the user via wireless communication protocol, such as cellular, Bluetooth, or radio means. It is noted that the user can set the various virtual fences and containment plan settings that consist of visual indicators, audible indicators, and/or physical stimulus on the GUI of a computing device by drawing the fenced boundaries on a map. The ease of visually indicating where virtual fences are to be placed allows for precise boundary placement that may not be possible with hotwires and electric fences.

While some embodiments statically set one or more virtual fences and adhere to the containment plan settings for each fence that are designated by the user, other embodiments can dynamically alter virtual fences and containment plan settings based on sensed and/or predicted animal behavior. The computing capability of the animal device alone allows for a user to provide a template containment plan, which may or may not include at least one virtual fence, that is modified autonomously by the local animal device controller based on the detected readings from one or more sensors. As an example, a virtual fence may be moved, or the containment settings may be modified, in response to the biologic status of the animal, as measured by sensors of the animal device, such as body temperature, heartrate, and oxygen saturation.

An animal device may also be configured to adapt to environmental conditions, such as outside temperature and humidity, to alter a virtual fence and/or containment setting. It is contemplated that the animal device is continuously or sporadically connected to a remote weather host, such as via a wireless pathway, to detect current or forecasted conditions that prompt changes in virtual fence and/or containment settings. The ability to adapt to existing and changing weather can protect an animal from various hazardous situations, such as lightning, flooding, and high winds, by changing a virtual fence to keep the animal from a tree, low lying elevation, or high elevation.

Figure 4:
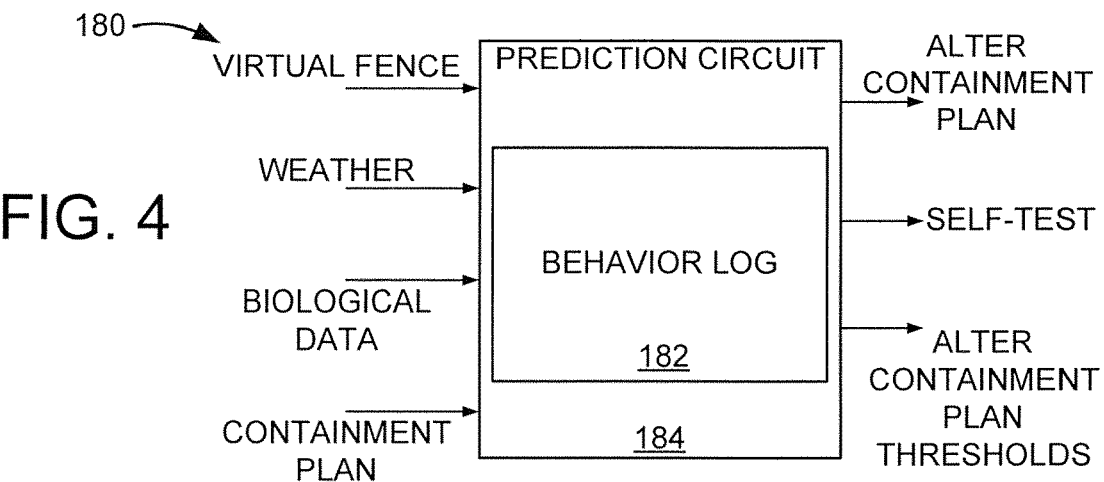
FIG. 4 shows a block representation of portions of an intelligent animal containment system arranged in accordance with assorted embodiments.

The computing power of the animal device may additionally adapt the location of virtual fences and containment plan settings in response to predicted animal behavior. FIG. 4 conveys an example prediction module 180 that can be incorporated into the intelligent animal device of FIG. 2 in some embodiments. The prediction module 180 can be stored and executed in local device memory where animal behavior is logged. It is noted that logged animal behavior may be continuously or sporadically monitored with less than all monitored behavior being temporarily, or permanently, stored in memory as a behavior log 182.

The stored animal conduct of the behavior log 182 is not limited to a particular parameter and can consist of multiple different metrics, such as biological and positional characteristics measured over time. The behavior log 182 is utilized by a prediction circuit 184 where at least the user-defined virtual fence(s), weather, biological readings from a biometric sensor, and template containment plan are inputted. The prediction circuit 184 analyzes the input parameters with respect to the previously occurring behavior of the behavior log 182 based on one or more algorithms to determine if any alteration to virtual fence location and/or containment plan can prevent unwanted future animal behavior.

The prediction circuit 184 can identify from the logged events when an animal is likely to replicate past events, such as sleeping locations, jumping a fence, digging under a fence, biting limbs from a tree, or swimming in a pool. The prediction circuit 184 may further predict behavior not previously encountered, such as reaction to severe weather like thunder. The ability to intelligently consult previous logged animal behavior from the behavior log 182 allows the prediction circuit 184 to generate likelihoods for various behaviors being repeated. Such likelihood calculations may have risk percentages that a user can set as thresholds for alteration of a virtual fence and/or containment plan. For instance, a greater than 80% risk of an identified behavior occurring triggers the animal device to adapt the virtual fence, such as by reducing the size or changing the shape of the fence boundary, or adapt the containment plan, such as by increasing physical stimuli or where stimuli begin being applied.

The prediction circuit 184 may detect behavior from the inputs and/or behavior log 182 that triggers the alteration of containment thresholds. A non-limiting example containment threshold alteration changes the refresh rate of logged behavior, clearing existing logged behavior from the log 182, calculating a reliability factor of predicted behavior, and adapting one or more prediction algorithms. By self-testing the performance of the prediction circuit 184, an animal containment system can maintain optimized operation with continual improvement in predicting an animal's behavior and reaction to events.

It is contemplated that the prediction circuit 182 may request input from a user to clarify certain logged events. For instance, logged animal behavior that appears to be an outlier that should be disregarded may be queried to a user to determine if any undetected parameters were present. The feedback from a user allows the prediction circuit 184 to logically eliminate and/or re-characterize logged behavior to improve the prediction of future animal behavior.

Figure 5:
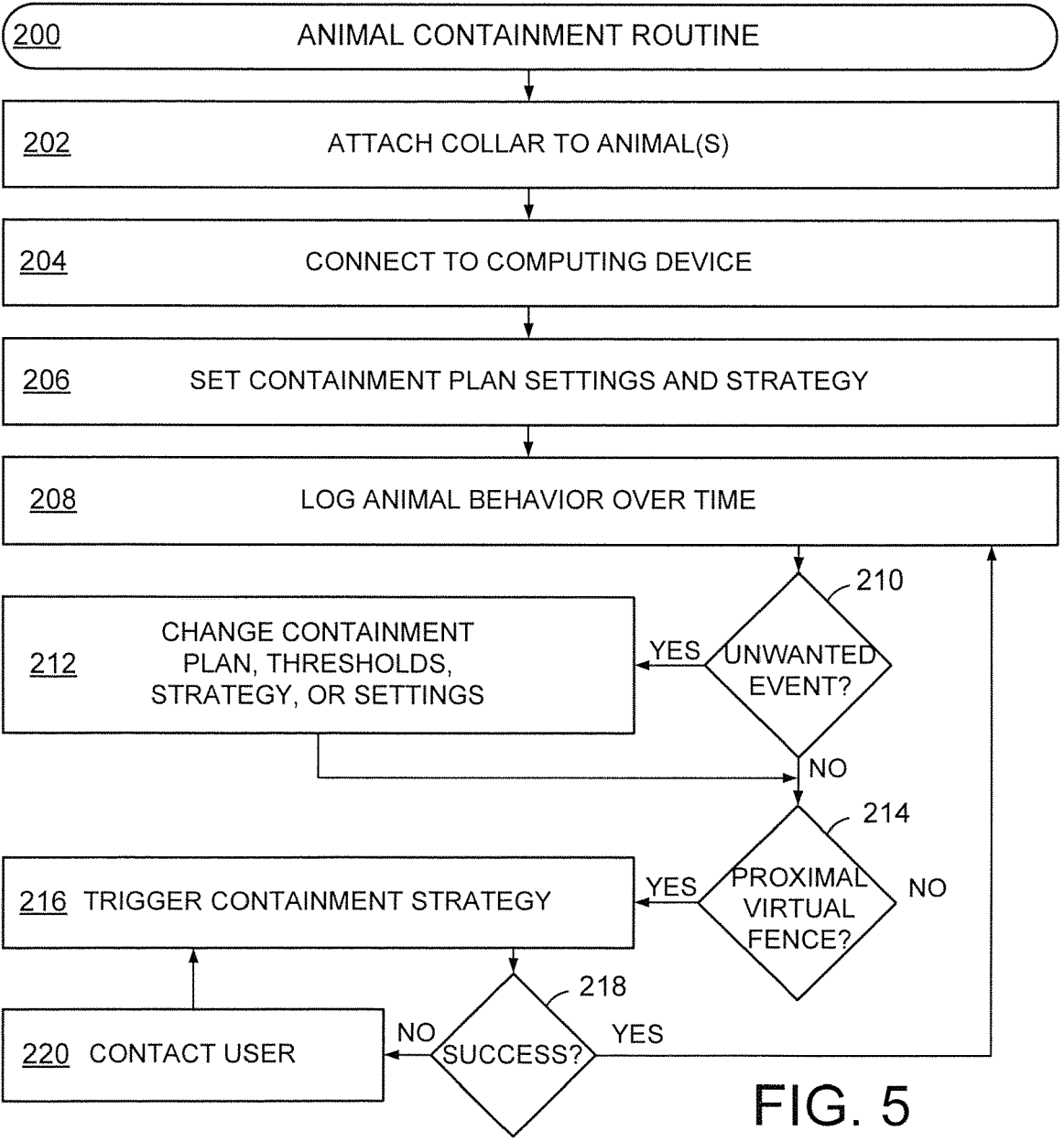
FIG. 5 is an animal containment routine that can be executed with the various embodiments of FIGS. 1-4.

In FIG. 5, an example animal containment routine 200 is provided that can utilize the various embodiments of FIGS. 2-4 in the environment of FIG. 1 in accordance with various embodiments. The routine 200 can begin by attaching one or more intelligent animal devices to at least one animal in step 202. It is contemplated that an animal may wear multiple separate devices, such as a collar and jacket, on different parts of its body, but such arrangement is not required. At least one animal device is attached in step 202 to multiple different animals, which may be of different species, such as a horse and a dog.

The device(s) attached in step 202 subsequently connect to a computing device in step 204 where at least one virtual fence and containment plan is loaded in step 206. Step 206 may further consist of a user selecting particular virtual fence locations, such as by drawing a geofence on a GUI, and particular containment settings, such as physical stimulus intensities and when to contact the user. Some embodiments concurrently operate multiple different virtual fences for a single animal while other embodiments concurrently operate different virtual fences and containment plan settings for different animals.

At predetermined intervals, such as every minute or second, step 208 proceeds to measure and record one or more behavior characteristics into a behavior log. As a result of the logged behavior characteristics, the position, biological condition, and weather may individually, or collectively, be stored in temporary animal device cache memory or permanently in non-volatile local memory. Either continually or sporadically, the behavior logged in step 208 can be used to predict future animal behavior with a prediction module of the animal device.

Decision 210 evaluates if a predicted animal behavior is likely to result in an unwanted event, such as harm to the animal or escape from the containment region. Such likelihood may correspond with a calculated risk factor that is evaluated with respect to user-defined thresholds. If an unwanted event is likely, step 212 intelligently adapts the containment plan settings, prediction thresholds, and/or virtual fence configuration in an attempt to prevent, or at least mitigate the extent of, the unwanted event.

At the conclusion of step 212, or if no unwanted event is predicted in decision 210, the routine 200 advances to decision 214 where the physical position of the animal(s) wearing an animal device are monitored. It is noted that decisions 210 and 214 may concurrently operate without limitation. The detection of an animal approaching, or crossing, a virtual fence boundary triggers step 216 to activate the corresponding portion of a containment plan designated by the user. For example, step 216 can begin a containment strategy that progressively applies visual, audible, and/or physical containment means via the animal device based on the animal's position relative to one or more virtual fences.

The goal of the containment strategy carried out in accordance with the containment plan settings is to return the animal to the predetermined containment region defined by the virtual fence. In the event the animal strays far beyond a virtual fence, the goal of the containment strategy may automatically alter to calm the animal and reduce further movement until the user is in close proximity to the animal device. Regardless of the goal of the containment strategy, decision 218 evaluates if the goal has been achieved. If so, step 208 is revisited. If not, a user is contacted in step 220. It is contemplated that the containment strategy is altered from redirecting an animal back to the containment region after step 220 to activating visual, audible, and/or physical stimuli to calm the animal and reduce movement.

Figure 6:
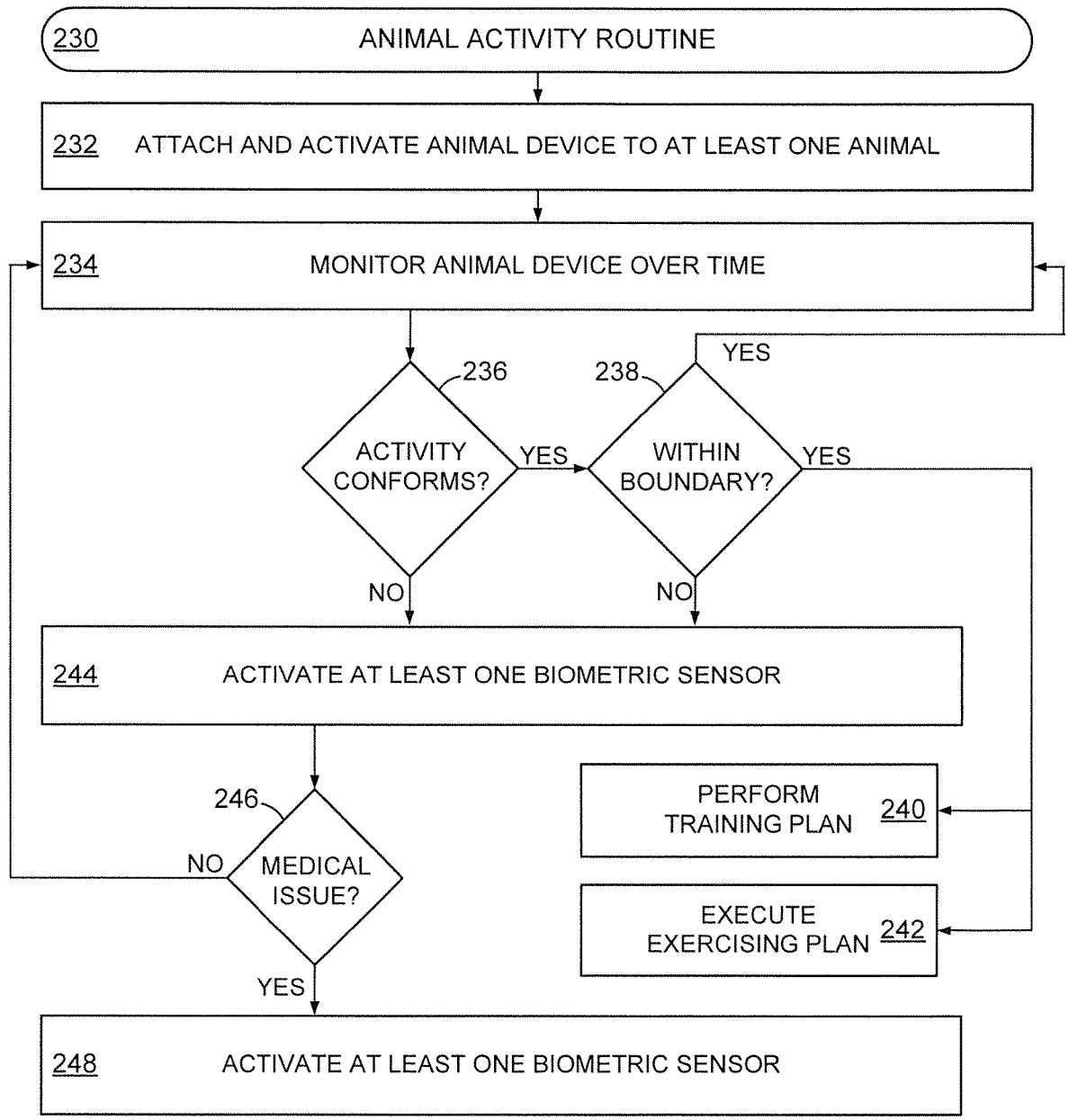
FIG. 6 provides an example animal activity routine conducted by the assorted embodiments of an intelligent animal containment system.

FIG. 6 is an example animal activity routine 230 that may be executed with the assorted embodiments of FIGS. 1-5 to intelligently monitor one or more animals within at least one containment area. Step 232 begins by activating at least one animal device that is attached to an animal. An animal device is monitored over time in step 234. Such monitoring may be continuous, or sporadic, and may partially, or completely be logged in local device memory.

At any time, decision 236 can evaluate if the activity of the animal detected in step 234 conforms to predetermined animal activity plans. That is, a user can establish any number of animal activity plans that choreograph an animal's behavior, such as exercise or position within a containment area, or medical condition, such as heartrate or body temperature. The choreographed behavior can allow the animal device to induce activities while an animal is within the containment area, which is confirmed in decision 238.

As a non-limiting example, decisions 236 and 238 can result in step 240 performing a training plan for the animal that consists of selected audio, visual, and electrical stimuli applied as directed by the animal device controller to correct a detected animal behavior, such as jumping, and/or correlating verbal commands to animal behavior, such as sitting, staying, fetching, and laying down. Detection of the animal within the containment area may also result in step 242 executing a predetermined exercising plan that can induce animal movement for a selected amount of time, distance, heartrate, body temperature, and time of day.

While a biometric sensor can be selectively activated and monitored by an animal device controller at any time, some embodiments activate at least one biometric sensor, such as a body temperature and heartrate monitor, in step 244 prior to evaluating the medical condition of the animal in decision 246. If a medical issue is identified in decision 246, step 248 proceeds to notify a human contact, such as via message, call, or audible alert. Step 248 may also execute one or more medical remedies, such as inducing the animal to stop moving, move the animal to shade, and play audible soothing sounds. In the event no medical issue is detected from decision 248, the routine 230 returns to step 234.

Through the utilization of an animal containment system, in accordance with various embodiments, one or more animals can be autonomously monitored, maintained, and controlled within a predetermined containment region. The ability to adapt user-defined virtual fences and containment plan settings based on detected and/or predicted animal behavior allows the animal containment system to intelligently respond to animal behavior and environmental events to prevent, or mitigate, unwanted consequences that can harm the animal. The incorporation of positional and biometric measurements into the animal containment system allows for a more complete analysis of the animal's behavior that can serve to better protect the animal from harm even if the animal does not approach or cross a virtual fence.

It is to be understood that even though numerous characteristics of various embodiments of the present disclosure have been set forth in the foregoing description, together with details of the structure and function of various embodiments, this detailed description is illustrative only, and changes may be made in detail, especially in matters of structure and arrangements of parts within the principles of the present technology to the full extent indicated by the broad general meaning of the terms in which the appended claims are expressed.

What is claimed is:
1. A method comprising:
activating an animal device attached to an animal;
detecting the animal being physically positioned outside of a first predetermined containment area with the animal device;
detecting a medical condition in the animal with at least one biometric sensor of the animal device; and
executing a containment strategy with a controller of the animal device, the containment strategy comprising activating a speaker of the animal device and conducting at least one medical remedy with the animal device to remediate the detected medical condition.
2. The method of claim 1, wherein the controller activates a visual indicator of the animal device in response to the detection of the animal being physically positioned outside of the first predetermined containment area.
3. The method of claim 2, wherein the controller concurrently activates the speaker and the visual indicator.
4. The method of claim 2, wherein the controller activates the visual indicator in response to the animal crossing a second predetermined containment area, the first predetermined containment area being different than the second predetermined containment area.
5. The method of claim 4, wherein the controller activates a stimulus module of the animal device in response to the detection of the animal being physically positioned outside of a third predetermined containment area.
6. The method of claim 1, wherein the first, second, and third containment areas are each non-symmetric.
7. The method of claim 1, wherein the controller contacts a user in response to the containment strategy not returning the animal to the first predetermined containment area.

8. The method of claim 1, wherein the controller activates the speaker to train a behavior in the animal while the animal device detects the animal is physically within the first predetermined area.

9. The method of claim 1, wherein the controller activates the speaker to induce the animal to exercise while the animal device detects the animal is physically within the first predetermined area.

10. The method of claim 1, wherein the controller alters the containment strategy based on a reading from the at least one biometric sensor of the animal device.

11. The method of claim 1, wherein the controller detects a medical issue with the animal with the at least one biometric sensor of the animal device and contacts a user.

12. A method comprising:
   activating an animal device attached to an animal;
   detecting a medical condition in the animal with at least one biometric sensor of the animal device;
   predicting the animal will physically cross a predetermined containment area with the animal device; and
   executing a containment strategy with a controller of the animal device, the containment strategy comprising activating a speaker of the animal device and conducting at least one medical remedy with the animal device to remediate the detected medical condition.

13. The method of claim 12, wherein the controller changes the containment strategy in response to an animal behavior predicted by the controller.

14. The method of claim 12, wherein the controller changes the predetermined containment area in response to lower a risk of an unwanted event from happening to the animal.

15. The method of claim 12, wherein the controller progressively activates the speaker and a stimulus module to prevent the animal from physically crossing the predetermined containment area.

16. The method of claim 12, wherein the controller utilizes at least one biometric sensor of the animal device to calm the animal with the speaker.

* * * * *